(12) United States Patent
Beck et al.

(10) Patent No.: US 7,707,895 B2
(45) Date of Patent: May 4, 2010

(54) METHOD AND DEVICE FOR TESTING THE STRENGTH OF A CONNECTION USING CENTRIFUGAL FORCE

(75) Inventors: Uwe Beck, Falkensee (DE); Georg Reiners, Berlin (DE); Christian Berndt, Berlin (DE); Sylke Grune, Chemnitz (DE); Rüdiger Uhlendorf, Dransfeld (DE)

(73) Assignee: BAM Bundesanstalt fur Material-Forschung und-Prufung, Berlin (DE)

( * ) Notice: Subject to any disclaimer, the term of this patent is extended or adjusted under 35 U.S.C. 154(b) by 105 days.

(21) Appl. No.: 11/667,586

(22) PCT Filed: Nov. 11, 2005

(86) PCT No.: PCT/EP2005/012351

§ 371 (c)(1),
(2), (4) Date: Oct. 16, 2007

(87) PCT Pub. No.: WO2006/050996

PCT Pub. Date: May 18, 2006

(65) Prior Publication Data

US 2008/0302190 A1    Dec. 11, 2008

(30) Foreign Application Priority Data

Nov. 11, 2004   (DE)   ............ 10 2004 055 621

(51) Int. Cl.
*G01N 3/08* (2006.01)
(52) U.S. Cl. .......................... 73/827; 73/834
(58) Field of Classification Search ............ 73/150 A, 73/827, 834
See application file for complete search history.

(56) References Cited

U.S. PATENT DOCUMENTS 3,290,929 A * 12/1966 Sheldon .................. 73/831
4,143,543 A    3/1979 Layden et al.

(Continued)

FOREIGN PATENT DOCUMENTS

DE    195 38 388 C2    4/1997

(Continued)

OTHER PUBLICATIONS

International Search Report dated Feb. 7, 2006.

*Primary Examiner*—Lisa M Caputo
*Assistant Examiner*—Freddie Kirkland, III
(74) *Attorney, Agent, or Firm*—Buchanan Ingersoll & Rooney PC

(57) ABSTRACT

The invention relates to a method for examining the resistance of a connection between two bodies, whereby one of the bodies only has a small mass. A correspondingly directed force is exerted upon the connection until disconnection thereof. The force used is the centrifugal force which acts at a distance from a rotational axis in a concentric manner about said rotated connection. Said method is particularly advantageous if the body having a small mass is a coating which is applied to the other body. In order to obtain a sufficiently high centrifugal force, an examining stamp is applied to the body having the small mass and/or the coating on the side oriented away from the connection. The adhesion between the body and/or the coating and the examining stamp is greater than between both of the bodies and/or the coating and the other body.

16 Claims, 2 Drawing Sheets

U.S. PATENT DOCUMENTS

Figure 2:
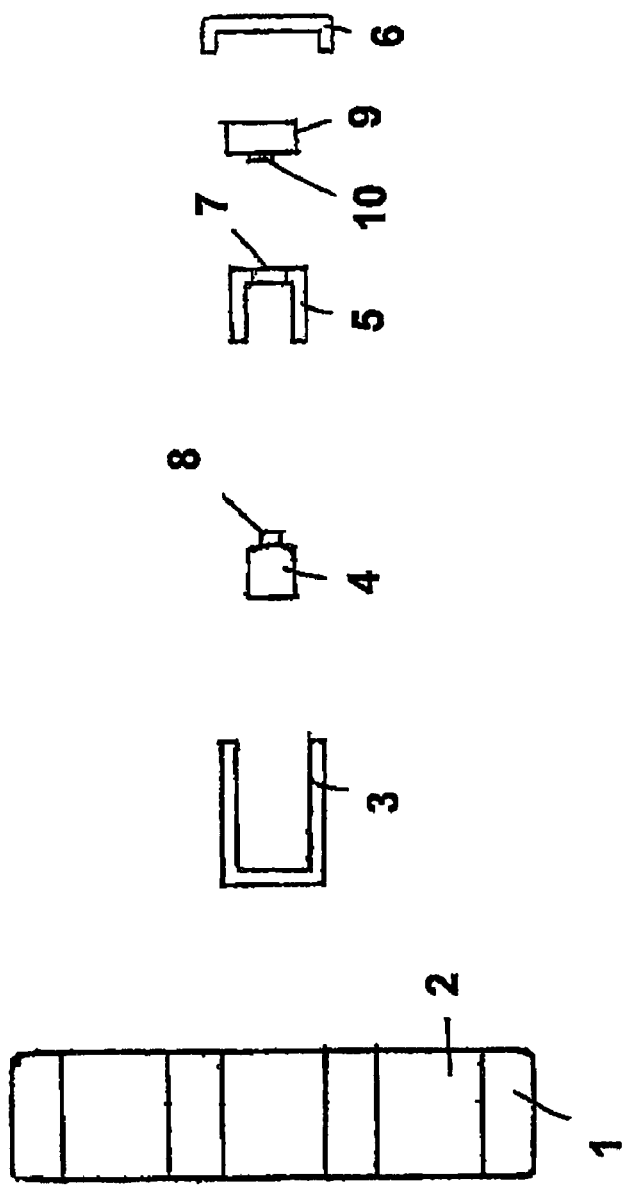

| | | | |
|---|---|---|---|
| 4,553,438 A | * 11/1985 | Dawson et al. | 73/830 |
| 4,856,326 A | * 8/1989 | Tsukamoto | 73/150 A |
| 4,991,444 A | * 2/1991 | Dodd | 73/788 |
| 6,158,277 A | * 12/2000 | Artzt et al. | 73/159 |
| 6,365,412 B1 | * 4/2002 | Feygin | 436/45 |

FOREIGN PATENT DOCUMENTS

| | | |
|---|---|---|
| JP | 3-287048 A | 12/1991 |
| JP | 5-249028 A | 9/1993 |
| JP | 11-64212 A | 3/1999 |
| JP | 11-258081 A | 9/1999 |
| JP | 2003-21592 A | 1/2003 |
| SU | 1126843 A | 11/1984 |

* cited by examiner

METHOD AND DEVICE FOR TESTING THE STRENGTH OF A CONNECTION USING CENTRIFUGAL FORCE

There are a number of methods for evaluating the adhesion of coatings. They are as diverse as the possible combinations of substrate and coating materials, depending on the relevant or necessary coating thicknesses and adhesion areas.

Multi-layer systems subject to extreme mechanical stress (disposable cutting inserts, substrate steel, for example), optical multi-layer systems (dielectric mirror, substrate glass, for example), electrical shields and conductors (mobile phone housing and conductor plates, substrate plastic, for example), optical and hermetised electro-platings (reflectors and packaging materials, substrate plastic as a mould and as a film) are to be mentioned as examples of the variety of possible applications.

Examples of relatively widespread methods for the evaluation of adhesion are, for example, the India rubber test (ISO 9211-4), the scratch test (DIN V ENV 1071-3, ISO 1518, ASTM D 2197), the pull-off test (ISO/DIS 4624, ASTM D 4541), the peel test (ASTM B 533, DIN 53494, DIN 58196-6, ISO 14676, DIN 53282, ISO 4578) and the Rockwell C test (DIN EN ISO 6508-1, VDI [Association of German Engineers] Directive 3198).

At the same time, adhesion (critical adhesive force for each surface) as a physical measure is determined only with the pull-off test, strictly speaking. A pull-off stud must be affixed for this purpose. It is then subjected to a pull-off test. However, the pull-off test is rarely used in practice for routine quality control, because it is always a single test, a logging pull-off testing device with double-gimbal suspension of substrate and pull-off stud is necessary, and reproducibility of the mounting in the pull-off testing device is critical. In addition, the information can be severely falsified if the transmission of force is slanting and non-linear, and therefore not constant throughout the lamination surface.

The other methods mentioned as examples merely classify the adhesion, for example in terms of critical standard loads in the scratch test or typical failure pattern with the Rockwell C test. In addition, with their very different types of stress, the use of the different methods is limited to particular applications. The scratch test and the Rockwell C test, for example, are suitable methods for hard material layers (hard layer on hard substrate), but they are not suitable for other applications (hard or soft layer on soft substrate, for example metal layers on plastic).

However, the tensile strength of spliced connections (adhesive connections, welded connections, soldered connections, bonded connections and pressed connections) is also routinely tested in pull-off testing devices. Here, the preparative effort is already included the product, which means the splice position itself; only a customized mount need be created. A double-gimballed suspension is also typically a requirement here.

One disadvantage of the familiar methods for testing the adhesion of coatings is that in all methods apart from the pull-off test, the adhesion is merely classified and cannot be established as a physical measure (numerical value with the unit of force per unit of area).

In addition, the individual tests are greatly customised to particular layer-substrate combinations. The India rubber test, for example, is used primarily for dielectric-optical coatings (filter, AR and HR systems), but practically not at all for metallic-optical coatings (reflectors) any longer.

All of the tests mentioned (even the pull-off test) are individual tests that are customised for (or must be adapted to) a specific layer-substrate combination (substrate material, layer material, layer thickness range, adhesion range). The variation in results is large for all tests and can reach 50% or more.

Using the pull-off test, the tensile strength of splice positions can be defined quantitatively as a physical measure (numerical value with the unit of force per unit of area), but only as an individual test, and under the assumption that bilateral mounting is possible. These requirements are often technical and economic exclusion criteria for micro-components.

As such, the object of this invention is to specify a method for testing the strength of a connection between two bodies, of which one body has a lesser mass, whereby an appropriately directed force is exerted against the connection until it fails, and the force is created by the centrifugal force acting on the connection spun in a concentric manner at a distance from a rotational axis, which enables a relatively large number of connections to be tested within a brief period with limited effort expended on the device, whereby the result of the test contains quantitative information in the form of a physical measurement relevant to adhesion or tensile strength (with the unit of force per unit of area).

Thus, a certification stamp is attached to the body of lesser mass on the side turned away from the connection in such a manner that the adhesion in the direction of the centrifugal force between the body of lesser mass and the certification stamp is greater than that between the body of lesser mass and the other body, and the mass of the body of lesser mass is increased for the test in a predetermined manner such that even relatively slow rotational speeds are sufficient to produce the centrifugal force necessary to break the connection. As such, a commercially-available table centrifuge can be used, for example, for the test of adhesion for a coating applied to a substrate. In this respect, a large number of different connections can be tested at the same time. The adhesion of a connection emerges from the centrifugal force when it breaks, which can be calculated as the sum of the masses of the separated bodies and of the certification stamp, the rotational speed and the distance from the rotational axis.

The invention is explained in greater detail below on the basis of an exemplary embodiment represented in the figures. They show in FIG. 1, a frontal view of the base plate for a mount for three test items, in FIG. 2, a cross-sectional exploded view of the base plate and the use of the mount element for a test item, and in FIG. 3, a block diagram of the production of a signal when a connection breaks, as well as the transmission and evaluation of this signal.

Figure 1:
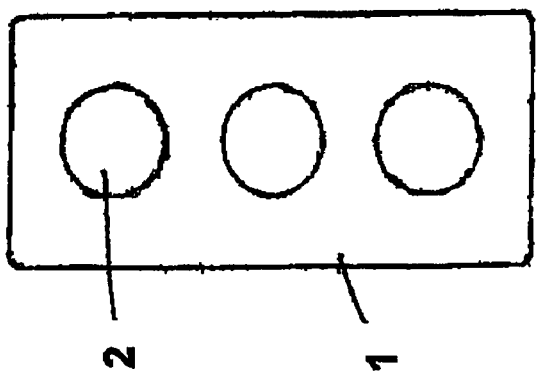

For example, the base plate 1 shown in FIG. 1 is attached to the inner wall of the drum rotor of a table centrifuge, whereby the holes 2, each of which serves to accept one mount element for one test item, are located above one another in the direction of the rotational axis of the rotor. There are multiple base plates 1 of this type (six, for example) attached rotationally symmetrical to its inner wall with fasteners or the like at identical and opposite intervals along the perimeter of the rotor.

According to FIG. 2, the mount elements for each single test item consist of an external beaker 3, a certification stamp 4, an internal beaker 5 and a cover 6.

The external beaker 3 is placed with a snug fit into a hole 2 of the base plate 1, is whereby it rests against the internal wall of the drum and protrudes from this opposite side over the base plate 1.

The internal beaker 5 contains a central hole 7 in its base, through which an appendage of the certification stamp 4 is pushed through. In addition to the beaker 5, the front face of the appendage 8 that projects through the hole 7 is bound to a coating 10 applied to a substrate 9 using a suitable adhesive over its entire surface. The unit consisting of the certification stamp 4, beaker 5 and test items 9 and 10 is then moved into the external beaker 3, and then the cover 6 is attached to the open end of the beaker 3.

Then, when all (or a portion, as required) of the holes 2 of all of base plate 1 are filled with the test items having mount elements, the test of the adhesion of the connections between the respective substrates 9 and the coatings 10 can be carried out by starting the rotation of the drum rotor of the centrifuge. If only a portion of the holes 3 contain a test item, one should take particular care to ensure that there is no imbalance.

As a result of the rotation of the drum rotor, the beaker 5 is held by the external beaker 3, and the substrate 9 is held by the beaker 5, and it effects a centrifugal force directed towards a cylindrical internal wall of the drum rotor as a pulling force on the connections between appendage 8 of the certification stamp 4 and coating 10 on one hand, and between coating 10 and substrate 9 on the other hand. Because the adhesion of the connection between coating 10 and substrate 9 is to be tested, it is to be ensured that the connection between appendage 8 and coating 10 resists higher pulling forces than the connection coating 10/substrate 9. The certification stamp 4 serves for the formation of sufficient centrifugal force, because the coating 10 alone does not have sufficient mass to produce the pulling force necessary for its detachment.

Depending on the adhesion of the coating 10 to the substrate 9, or the tensile strength of a spliced connection, the failure of the connection will occur at a given rotational radius at a particular rotational speed, which means the detachment of the combination consisting of certification stamp 4 and coating 10 from the substrate 9, or the separation of the two bodies bound by means of the spliced connection. This rotational speed can be determined electrically (as an imbalance event) along with each rotor position by means of special detection systems (electrical, electronic, optical or acoustic), and by doing so can be associated with the relevant test item without the need to interrupt the test for the other test items.

However, is should ensured that the resulting imbalance at the time of the detachment is not too great, and that it remains within the range of acceptability for imbalance correction for the respective centrifuge. This also means that the resulting flight paths and impingement forces at the time of failure must be kept to a minimum. However, they must still be great enough that the failure can be detected unambiguously.

The result of the test represents a quantitative conclusion in the form of a physical measure relevant to the adhesion or tensile strength (with the unit of force per unit of area).

In general, the centrifugal force $F_z$ must be greater than the bond strength $F_H$ of the coating or the adhesive strength $F_K$ of the spliced connection between the two bodies, so that a separation between coating and substrate (or between two bodies) occurs.

$$F_z > F_H \text{ or } F_K$$

Preliminary trials with pull-off tests yielded a maximum adhesive strength of $\sigma_{K,max}=50$ N/mm² for connections with high-performance adhesives.

If this acts on a spliced surface of approximately 7 mm² for example, the result in this case is a maximum adhesive strength of $$F_{H,max}=350 \text{ N}$$

At a certification stamp mass of m=2.5 g and a maximum centrifugal acceleration of approximately $a_{max}=16,400$ g, the effective maximum centrifugal force in a normal table centrifuge is:

$$F_{z,max}=m \cdot a_{max}=0.025 \text{ kg} \cdot 16,400 \cdot 9.81^{m}/_{s^2}=400 \text{ N}$$

Thus, in this example, spliced bonds with adhesion of not more than 50 N/mm² can be tested. However, the testing of spliced bonds is not limited to this range in principle; instead, the maximum testable adhesion emerges here from the performance of the centrifuge, which means the maximum centrifugal force achievable.

If one also assumes that the adhesive connection between the certification stamp 4 and the coating 10 has an adhesion of 50 N/mm², and also accepts that the connection surfaces between certification stamp 4 and coating 10, and between coating 10 and substrate 9, are the same, then all coatings with adhesion less than 50N/mm² can be tested. This applies in particular to all layers applied to a glass substrate by means vapour deposition.

However, using the indicated device it is also possible to realise not just pulling force, but also a combination of pulling forces and shearing forces, or even mere shearing force, that act upon the connection. For this purpose, the surface of the connection to be tested is arranged diagonally or even perpendicular to it, instead of parallel to the path tangent. In the prior art, testing devices of this type are extremely costly, even though there are often demands for combinations of pulling forces and shearing forces in practice. In this device, only the element is to be replaced. When using different elements, connections can be simultaneously subjected to pure pulling force, pure shearing force, and arbitrary combinations of pulling forces and shearing forces.

Figure 3:
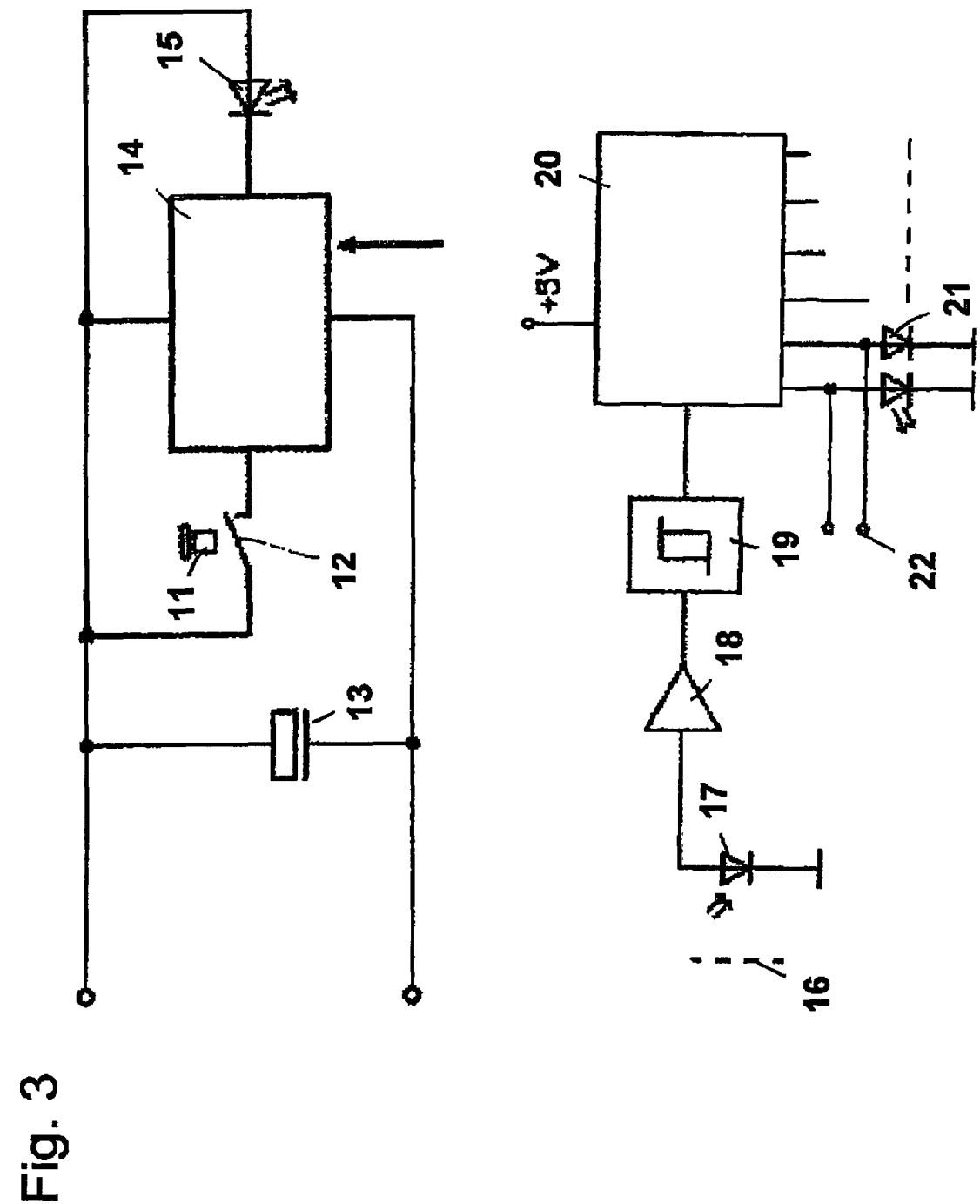

FIG. 3 shows a circuit for the production and transmission of a signal that indicates the failure of a connection in the upper part, as well as the circuit for the reception and analysis of this signal in the lower part. The upper part is located in the drum of a centrifuge, and the lower part is stationary and outside of the drum. The signal transmission is wireless between the two parts, by means of infrared beams for example.

When the connection between the two bodies of a test item 11 fails, a circuit 12 is closed, whereby a capacitor 13 is discharged. The current that flows over an encoded circuit 14 as a result activates the production of a signal that is directed to an infrared LED that delivers the appropriate infrared signal.

The infrared signal reaches an infrared sensor 17 via an infrared filter 16, and the electrical signal produced by it is led to a trigger switch 19 via an amplifier 18. The trigger impulse emitted by it is entered into a decoder 20. Its output signals cause the activation of LEDs 21 for indicating the failure event, and can be led to a logic circuit (not shown) associated with connectors 22 for the numerical analysis of the testing process. The circuit shown has the advantage of low energy use because a current flows only when the failure event occurs. Therefore, a capacitor is sufficient as an energy source, such that no leads for the delivery of energy to the drum are needed during the testing process. In addition, the use of infrared beams for the signal transmission also results in very limited power consumption.

With appropriate programming, almost any ramps (accelerations and decelerations) and changing force cycles can be realised. This is of particular importance for the fatigue test.

Finally, there is also the option of producing desired climate conditions for the test item. The design of the centrifuge drums as a climate chamber with the option of setting temperature and humidity requires only a relatively limited additional expense for a table centrifuge.

The invention claimed is:

1. Method for testing the strength of a connection between two bodies, of which one body has a lesser mass, whereby an appropriately directed force is exerted against the connection until it fails, and the force is created by the centrifugal force of a centrifuge including a drum rotor acting on the connection and spun in a concentric manner at a distance from a rotational axis, wherein a certification stamp is applied to the body of lesser mass on a side face of the connection in a manner such that an adhesion in the direction of the centrifugal force between the body of lesser mass and the certification stamp is greater than that between the body of lesser mass and the other body.

2. Method according to claim 1, wherein only the other body facing the rotational axis when viewed from the connection is held against a motion in the direction of the centrifugal force.

3. Method according to claim 1 wherein the body of lesser mass is a coating applied to the other body.

4. Method according to claim 1, wherein the connection between the two bodies is flat and runs at an angle between of 0 and 90 to the centrifugal force.

5. Method according to claim 1, wherein the failure of the connection is determined electrically.

6. Method according to claim 5, wherein the failure of the connection causes the discharge of a capacitor.

7. Method according to claim 5, wherein the signal indicating the failure of the connection is transmitted wirelessly to an analysis unit.

8. Method according to claim 1, wherein the level and speed of change of the force affecting the connection can be changed in a desired manner.

9. Method according to claim 1, wherein the connection is exposed to desired climate conditions.

10. Device for carrying out the method according to claim 1, wherein multiple test items are distributed on a cylindrical internal wall of the centrifuge's drum rotor concentric to the rotational axis, with one connection to be tested in the circumferential direction in each case, and/or placed above one another in the direction of the rotational access.

11. Device according to claim 10, wherein retaining bodies, each with at least one drilled hole running in the radial direction of the drum motor for retaining an element for mounting a test item, are placed rotationally symmetrical in the circumferential direction on the internal wall of the drum rotor of a centrifuge.

12. Device according to claim 11, wherein each retaining body has several drilled holes located above one another in the direction of the rotational axis.

13. Device according to claim 11, wherein the element consists of an external beaker held in the drilled hole and fixed in a radial direction of the drum rotor by its rotation, and an internal beaker held concentrically in the external beaker and fixed in its radial direction by the external beaker by rotating the drum rotor.

14. Device according to claim 13, wherein the test item is held in it by means of an opening designed into the base of the internal beaker.

15. Device according to claim 14, wherein the test item consists of a substrate provided with a coating, which is located on one side of the opening, and which has a certification stamp on the other side of the opening within the internal beaker, which is permanently bound to the coating by engagement through the opening.

16. Device according to claim 10, wherein it is designed as a table centrifuge.

* * * * *